US00PP26191P3

(12) United States Plant Patent
Egger

(10) Patent No.: US PP26,191 P3
(45) Date of Patent: Dec. 1, 2015

(54) ***SEDUM* PLANT NAMED 'MARINA'**

(50) Latin Name: ***Sedum telephium* (Syn. *Hylotelephium telephium*)**
Varietal Denomination: Marina

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 174 days.

(21) Appl. No.: 13/987,663

(22) Filed: Aug. 20, 2013

(65) Prior Publication Data

US 2015/0059039 P1 Feb. 26, 2015

(51) Int. Cl.
*A01H 5/02* (2006.01)

(52) U.S. Cl.
USPC ..... Plt./479

(58) Field of Classification Search
USPC ..... Plt./479
See application file for complete search history.

(56) References Cited

PUBLICATIONS

New Plants and Flowers, Jun. 14, 2013.*

* cited by examiner

*Primary Examiner* — Keith O. Robinson
(74) *Attorney, Agent, or Firm* — Klarquist Sparkman, LLP

(57) ABSTRACT

A new and distinct hybrid of *Sedum* plant substantially as shown and described, characterized by rose red flowers from pink buds, blue green leaves tinted lavender in the summer, rose pink stems, red carpels when the seed is developing, a dense, spreading habit, and excellent vigor.

2 Drawing Sheets

Botanical denomination: *Sedum telephium* (Syn. *Hylotelephium telephium*).
Variety designation: 'Marina'.

BACKGROUND OF THE INVENTION

The present invention relates to a new and distinct cultivar of *Sedum telephium* and given the cultivar name of 'Marina'. *Sedum* is in the family Crassulaceae. The new cultivar is part of a planned breeding program to make short, compact, multicrown plants. The new cultivar originated from an open pollinated seed picked from *Sedum* 26-5, a proprietary seedling.

Compared to the seed parent, *Sedum* 26-5, the new cultivar has a much better habit and longer, larger leaves.

Compared to *Sedum* 'Yellow Xenox', U.S. Plant Pat. No. 21,528, the new variety is has rose red flowers rather than pink, blue green leaves rather than yellow green, and a wider habit with more crowns from young plants (an advantage to a nursery grower as the plants fill the pots quickly).

This new and unique *Sedum* is distinguished by:

1. rose red flowers from pink buds,
2. blue green leaves tinted lavender in the summer,
3. rose pink stems,
4. red carpels when the seed is developing,
5. a dense, spreading habit, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the foliage of a 3 year old *Sedum* 'Marina' growing in the trial bed in early June in Canby, Oreg.

FIG. 2 shows a close up the inflorescence of *Sedum* 'Marina' in bud in early July.

DETAILED PLANT DESCRIPTION

Figure 3:
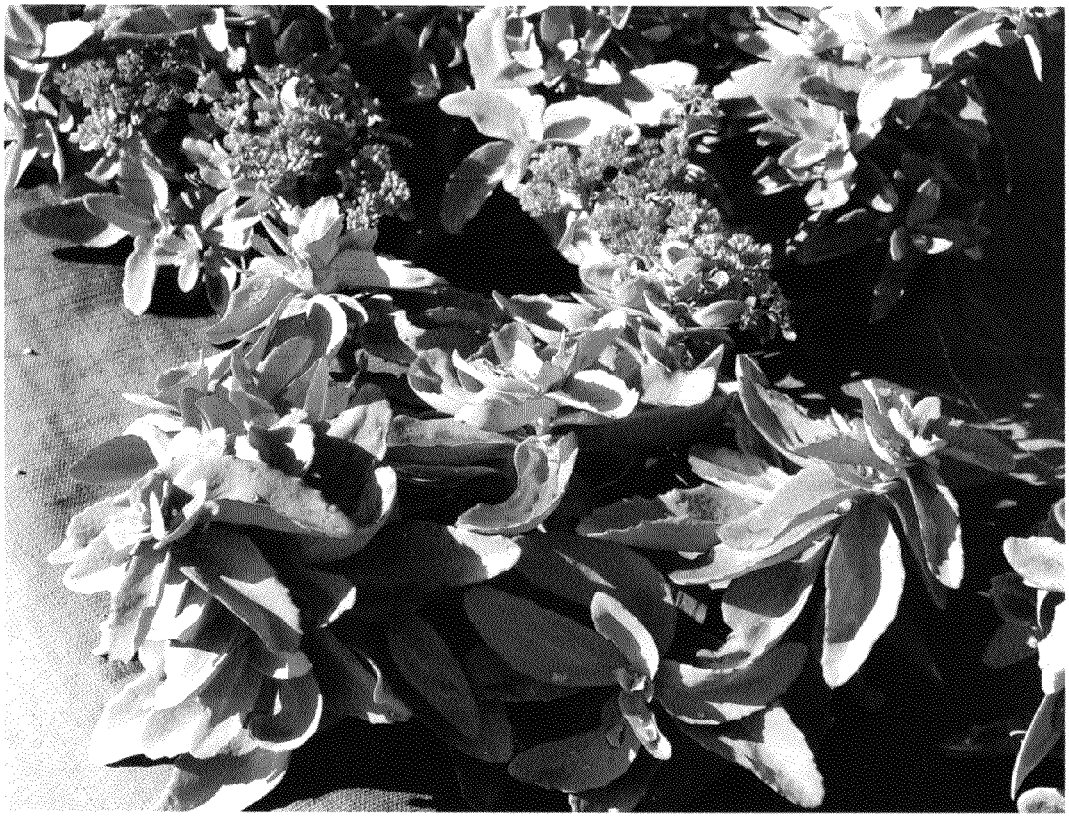
FIG. 3 shows one year old plants of *Sedum* 'Marina' in bloom in the trial field in late August in Canby, Oreg.

The following is a detailed description of the new *Sedum* hybrid based on observations of one year old specimens grown in the trial bed in full sun under typical outdoor conditions in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The Royal Horticultural Society Colour Chart, 5$^{th}$ edition, 2007.

Plant:

*Type*.—Herbaceous perennial.
*Hardiness*.—USDA Zone 4 to 9.
*Size*.—10 cm tall from the ground to the base of the inflorescence and 35 cm wide.
*Habit*.—Low, clumping mound.
*Vigor*.—Excellent.
*Roots and rooting*.—Main roots thick, with secondary roots dense and fibrous, color closest to Brown N200C in color; plants initiate roots in 10 days and produce a rooted plant in 4 weeks.

Stem:

*Number*.—About 6.

*Size*.—10 cm long and 7 mm wide.

*Internode length*.—2 mm to 20 mm long.

*Color*.—Yellow Green 146b in shade and Greyed Purple 187A in sun.

*Texture*.—Succulent.

*Surface*.—Glabrous.

Leaf:

*Type*.—Simple.

*Arrangement*.—Opposite.

*Shape*.—Oblong.

*Apex*.—Obtuse.

*Base*.—Obtuse.

*Venation*.—Pinnate, topside main vein Greyed Green 191A at base, bottom side main vein Yellow Green 148C.

*Margins*.—Irregularly serrate.

*Blade size*.—Grows to 10 cm long and 4 cm wide.

*Surface*.—Glabrous and matte on both sides.

*Texture whole leaf*.—Thick, spongy, succulent.

*Petiole*.—Leaves sessile.

*Leaf color*.—Topside Greyed Green 189A with purple tints Greyed Purple N187A in summer; bottom side Greyed Green 191A.

Inflorescence:

*Type*.—Terminal, corymbose, umbel-like.

*Number of flowers*.—About 300 per stem (increases with age).

*Pedicels*.—2 mm to 3 mm long, 1 mm wide, glabrous, closest to Greyed Green 197A.

*Peduncle*.—Grows to 2 cm tall and 4 mm wide, Greyed Purple 183A.

*Size*.—Grows to 10.5 cm deep and 10 cm wide.

*Bloom period*.—August through September in Canby, Oreg.

Flower bud:

*Size*.—2.5 mm wide, 3 mm deep.

*Description*.—Ovoid.

*Color*.—Greyed Purple 186C.

Flower:

*Type*.—Actinomorphic.

*Shape*.—Stellate.

*Size*.—4 mm deep and 4 mm wide.

*Corolla description*.—4 mm deep and 4 mm wide, 5 petals, each lanceolate, 4 mm long and 1.5 mm wide, margins entire, tip acuminate, glabrous on both sides, top side Greyed Purple 186C on top ⅔ and Greyed Purple 186D on bottom ⅔; bottom side Greyed Purple 186C.

*Calyx description*.—2 mm deep and 2.5 mm wide, stellate, 5 lobes, divided to the base, margins entire, tip acute, glabrous, Greyed Green 197A on both sides.

*Stamen description*.—10 in number, 3 mm long, filaments 3 mm long and Greyed Purple 187A, anthers sterile and reduced, no pollen.

*Pistil description*.—5 separate prominent carpels, each 4 mm deep and 1.5 mm wide, Red Purple 64A, style 1 mm long, stigma and style Greyed Purple 187A.

*Fragrance*.—None.

*Lastingness*.—Each stem lasts up to a month.

Fruit:

*Type*.—Ventrally dehiscent follicle, erect, attenuate.

*Fertility*.—Low.

*Size*.—3 mm wide and 3 mm deep.

*Color*.—Greyed Purple 187A.

Seed: None seen.

Disease and pest resistance or tolerance: Pest and disease resistance are typical for this type of *Sedum*.

I claim:

1. A new and distinct hybrid of *Sedum* plant as herein illustrated and described.

* * * * *

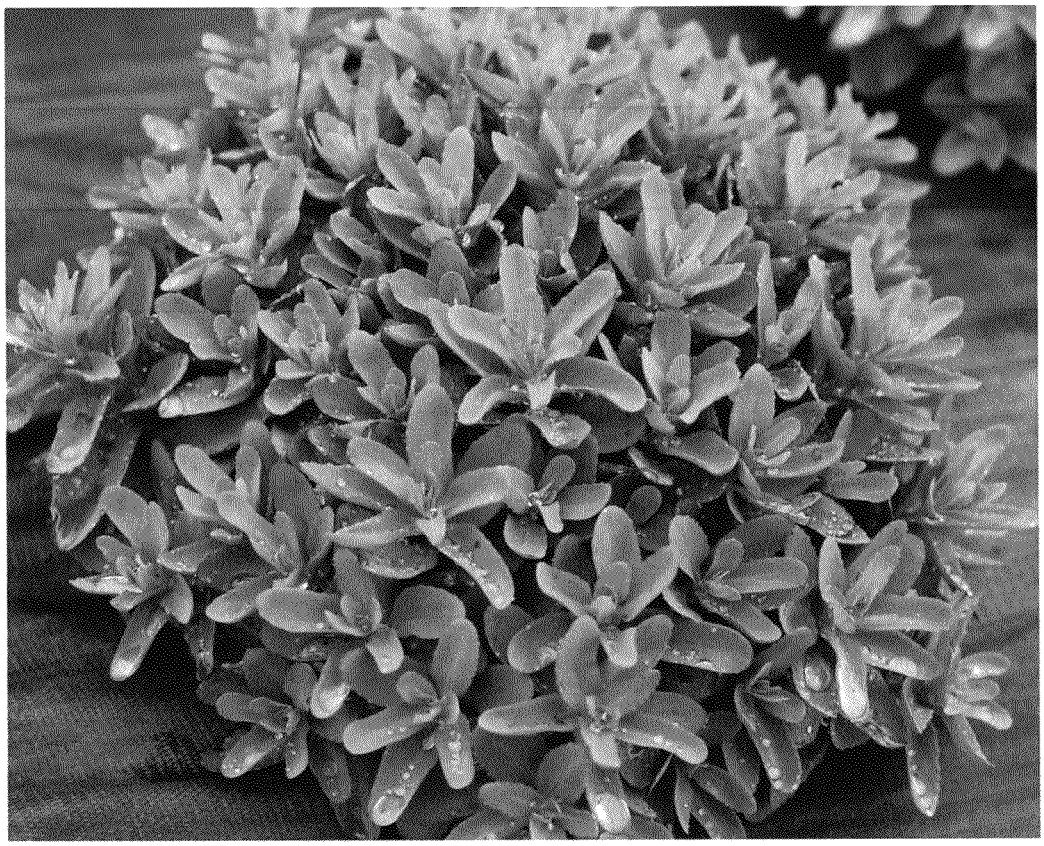
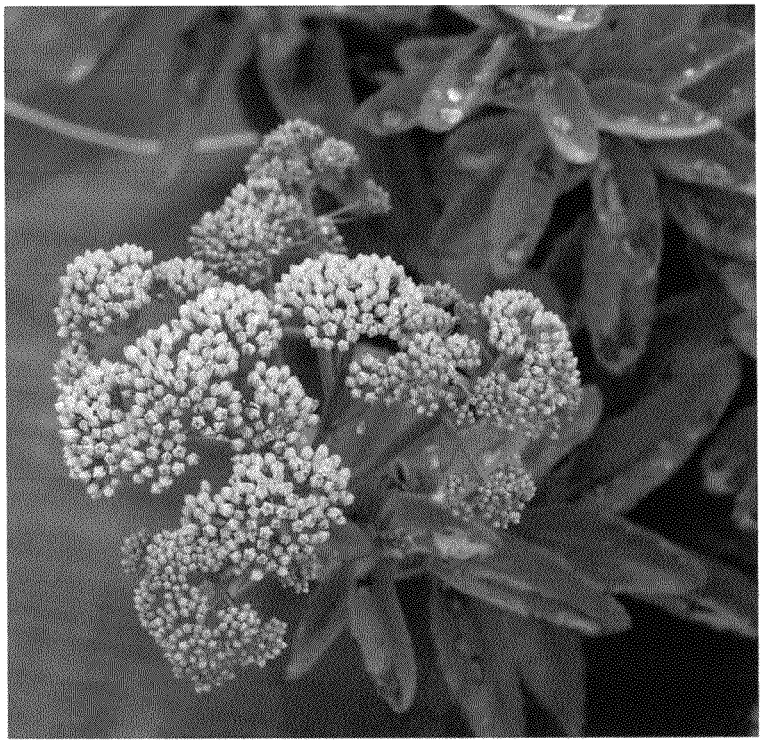
FIG. 1 above
FIG. 2 on left